(12) United States Patent
Crear et al.

(10) Patent No.: US 10,379,063 B2
(45) Date of Patent: Aug. 13, 2019

(54) DAMAGED APPLICATOR IDENTIFIER SYSTEM FOR ADDITIVE MANUFACTURING SYSTEM

(71) Applicant: General Electric Company, Schenectady, NY (US)

(72) Inventors: Donnell Eugene Crear, Simpsonville, SC (US); Tiffany Muller Craft, Simpsonville, SC (US); Kassy Moy Hart, Greenville, SC (US); Mikhail Pavlov, Dietikon (CH); Felix Martin Gerhard Roerig, Baden (CH); Dean Andrew Snelling, Greenville, SC (US)

(73) Assignee: General Electric Company, Schenectady, NY (US)

( * ) Notice: Subject to any disclaimer, the term of this patent is extended or adjusted under 35 U.S.C. 154(b) by 148 days.

(21) Appl. No.: 15/619,775

(22) Filed: Jun. 12, 2017

(65) Prior Publication Data

US 2018/0356350 A1    Dec. 13, 2018

(51) Int. Cl.

| | |
|---|---|
| *G06K 9/00* | (2006.01) |
| *G01N 21/956* | (2006.01) |
| *B05C 17/005* | (2006.01) |
| *B28B 11/08* | (2006.01) |
| *B28B 19/00* | (2006.01) |
| *G01N 21/95* | (2006.01) |
| *G05D 9/12* | (2006.01) |
| *G06T 7/00* | (2017.01) |
| *B33Y 40/00* | (2015.01) |
| *B29C 64/30* | (2017.01) |
| *G01N 21/88* | (2006.01) |
| *B33Y 30/00* | (2015.01) |

(Continued)

(52) U.S. Cl.
CPC . *G01N 21/95607* (2013.01); *B05C 17/00516* (2013.01); *B28B 11/0845* (2013.01); *B28B 19/0015* (2013.01); *B29C 64/30* (2017.08); *B29C 64/393* (2017.08); *B33Y 30/00* (2014.12); *B33Y 40/00* (2014.12); *G01N 21/8851* (2013.01); *G01N 21/9515* (2013.01); *G05D 9/12* (2013.01); *G06T 7/001* (2013.01); *B22F 3/1055* (2013.01); *B22F 2003/1056* (2013.01); *G01N 2021/8887* (2013.01)

(58) Field of Classification Search
CPC combination set(s) only.
See application file for complete search history.

(56) References Cited

U.S. PATENT DOCUMENTS

| | | | |
|---|---|---|---|
| 6,651,303 | B1 | 11/2003 | Toivanen et al. |
| 8,083,513 | B2 | 12/2011 | Montero-Escuder et al. |

(Continued)

*Primary Examiner* — Alex Kok S Liew
(74) *Attorney, Agent, or Firm* — Dale Davis; Hoffman Warnick LLC (57) ABSTRACT

A damaged applicator identifier system for an additive manufacturing (AM) system, and AM system including the same are disclosed. The damaged applicator identifier system may include a damaged applicator identifier determining whether the active applicator is damaged by identifying a non-planar surface in a layer of raw material on a build platform of the AM system after formation of the layer by the active applicator. A damaged applicator controller is configured to cause replacement or repair of the damaged, active applicator in response to the damaged applicator identifier identifying the damaged, active applicator.

20 Claims, 6 Drawing Sheets

(51) Int. Cl.
*B29C 64/393* (2017.01)
*B22F 3/105* (2006.01)

(56) References Cited

U.S. PATENT DOCUMENTS

| | | | |
|---|---|---|---|
| 8,366,432 B2 | 2/2013 | Perret et al. | |
| 2008/0131540 A1* | 6/2008 | Perret | B22F 3/1055 425/63 |
| 2011/0156304 A1* | 6/2011 | Walker | B23P 15/24 264/219 |
| 2016/0121397 A1 | 5/2016 | Aydin et al. | |
| 2016/0159011 A1* | 6/2016 | Marchione | B29C 64/386 700/98 |
| 2016/0236414 A1* | 8/2016 | Reese | G05B 19/4099 |

* cited by examiner

DAMAGED APPLICATOR IDENTIFIER SYSTEM FOR ADDITIVE MANUFACTURING SYSTEM

CROSS-REFERENCE TO RELATED APPLICATIONS

This application is related to U.S. application Ser. No. 15/619,772, filed concurrently and currently pending.

BACKGROUND OF THE INVENTION

The disclosure relates generally to additive manufacturing, and more particularly, to a damaged applicator identifier system for an additive manufacturing (AM) system and an AM system including the damaged applicator identifier system.

Additive manufacturing (AM) includes a wide variety of processes of producing an object through the successive layering of material rather than the removal of material. As such, additive manufacturing can create complex geometries without the use of any sort of tools, molds or fixtures, and with little or no waste material. Instead of machining components from solid billets of material, much of which is cut away and discarded, the only material used in additive manufacturing is what is required to shape the object.

Additive manufacturing techniques typically include taking a three-dimensional computer aided design (CAD) file of the object to be formed, electronically slicing the object into layers, e.g., 18-102 micrometers thick, and creating a file with a two-dimensional image of each layer, including vectors, images or coordinates. The file may then be loaded into a preparation software system that interprets the file such that the object can be built by different types of additive manufacturing systems. In 3D printing, rapid prototyping (RP), and direct digital manufacturing (DDM) forms of additive manufacturing, material layers are selectively dispensed, sintered, formed, deposited, etc., to create the object.

In metal powder additive manufacturing techniques, such as direct metal laser melting (DMLM) (also referred to as selective laser melting (SLM)), metal powder layers are sequentially melted together to form the object. More specifically, fine metal powder (raw material) layers are sequentially melted after being uniformly distributed using an applicator on a metal powder bed or build platform. The metal powder build platform can be moved in a vertical axis. The process takes place in a processing chamber having a precisely controlled atmosphere of inert gas, e.g., argon or nitrogen. Once each layer is created, each two dimensional slice of the object geometry can be fused by selectively melting the metal powder. The melting may be performed by a melting beam source such as an electron beam or a high powered laser (in latter case, e.g., a 100 Watt ytterbium laser), to fully weld (melt) the metal powder to form a solid metal. The melting beam moves in the X-Y direction using, e.g., scanning mirrors, and has an intensity sufficient to fully weld (melt) the metal powder to form a solid metal. The metal powder build platform is lowered for each subsequent two dimensional layer, and the process repeats until the object is completely formed. In order to create certain larger objects faster, some metal additive manufacturing systems employ two or more high powered melting beam sources that work together to form an object.

In metal powder AM systems, an applicator, sometimes referred to as a recoater or wiper, is used to apply each thin layer of raw material, e.g., metal powder, over the build platform and any previously formed layers of the object. Each applicator includes an applicator element in the form of a lip, brush, blade or roller made of metal, plastic, ceramic, carbon fibers or rubber that spreads the metal powder evenly over the build platform. An active or primary applicator is used to start the build. Because the applicator element is oftentimes made from a softer material than the actual manufacturing material, it is susceptible to damage during use. A damaged applicator may have a defect in the form of a misalignment with the build platform or some sort of defective shape in its applicator element that is transferred into the next layer of raw material applied to the build platform. In any event, the melting beam source subsequently prints the defect into the object. For example, a defective shape in the applicator element can take a variety of forms such as a ridge, ripple, bump, etc., in the layer of raw material. If a defective shape occurs during use, the defective shape will be continuously wiped into the metal powder and the melting beam source will solidify this area as a repeating defect in the object. In order to address this challenge, some current systems change the applicator element between AM system uses, which may require an unscheduled work stoppage and may prolong the use of a damaged applicator until an effective stopping point is reached in the process. Alternatively, some current systems employ either replacement applicators or replaceable applicator elements to replace a damaged applicator when damage is identified on the applicator element, e.g., during use of the AM system. Current systems that identify damage to the applicator element do so by direct analysis of the applicator element or by indirect analysis of drag forces on the applicator experienced by the transport system that moves the applicator.

BRIEF DESCRIPTION OF THE INVENTION

A first aspect of the disclosure provides a damaged applicator identifier system for an additive manufacturing (AM) system, the damaged applicator identifier system comprising: a damaged applicator identifier configured to determine whether an active applicator is damaged by identifying a non-planar surface in a test layer of raw material on a build platform of the AM system after formation of the test layer by the active applicator; and a damaged applicator controller configured to cause replacement or repair of the damaged, active applicator in response to the damaged applicator identifier identifying the damaged, active applicator.

A second aspect of the disclosure provides an additive manufacturing (AM) system, comprising: a build platform; a melting beam source for sequentially building an object layer by layer on the build platform; a raw material source operatively coupled to the build platform for providing raw material to the build platform for the sequential building; an applicator system operative to apply a layer of the raw material on the build platform from the raw material source using an active applicator; a damaged applicator identifier configured to determine whether an active applicator is damaged by identifying a non-planar surface in a test layer of raw material on a build platform of the AM system after formation of the test layer by the active applicator; and a damaged applicator controller configured to cause replacement or repair of the damaged, active applicator in response to the damaged applicator identifier identifying the damaged, active applicator.

A third aspect of the disclosure provides an additive manufacturing (AM) system, comprising: a build platform; a melting beam source for sequentially building an object layer by layer on the build platform; a raw material source operatively coupled to the build platform for providing raw material to the build platform for the sequential building; an applicator system operative to apply a layer of the raw material on the build platform from the raw material source, the applicator system including a plurality of applicators including an active applicator and at least one replacement applicator for replacing a damaged, active applicator, each replacement applicator including an undamaged applicator element; a damaged applicator identifier configured to determine whether an active applicator is damaged by identifying a non-planar surface in a test layer of raw material on a build platform of the AM system after formation of the test layer by the active applicator; and a damaged applicator controller configured to cause replacement or repair of the damaged, active applicator in response to the damaged applicator identifier identifying the damaged, active applicator.

The illustrative aspects of the present disclosure are designed to solve the problems herein described and/or other problems not discussed.

BRIEF DESCRIPTION OF THE DRAWINGS

These and other features of this disclosure will be more readily understood from the following detailed description of the various aspects of the disclosure taken in conjunction with the accompanying drawings that depict various embodiments of the disclosure, in which:

FIG. 7 shows a schematic top view and

FIG. 9 shows a schematic top view and

FIG. 11 shows a schematic top view and

FIG. 12 shows a schematic side view of an applicator system including a repair device to repair a damaged applicator according to an embodiment of the disclosure.

FIG. 13 and FIG. 14 show side views of alternative embodiments of a repair device to repair a damaged applicator according to an embodiment of the disclosure.

It is noted that the drawings of the disclosure are not to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

As indicated above, the disclosure provides a damaged applicator identifier system for an additive manufacturing (AM) system, and an AM system including the same. The damaged applicator identifier system may include a damaged applicator identifier determining whether the active applicator is damaged by identifying a non-planar surface in a layer of raw material on a build platform of the AM system after formation of the layer by the active applicator. A damaged applicator controller is configured to cause replacement or repair of the damaged, active applicator in response to the damaged applicator identifier identifying the damaged, active applicator.

Figure 1:
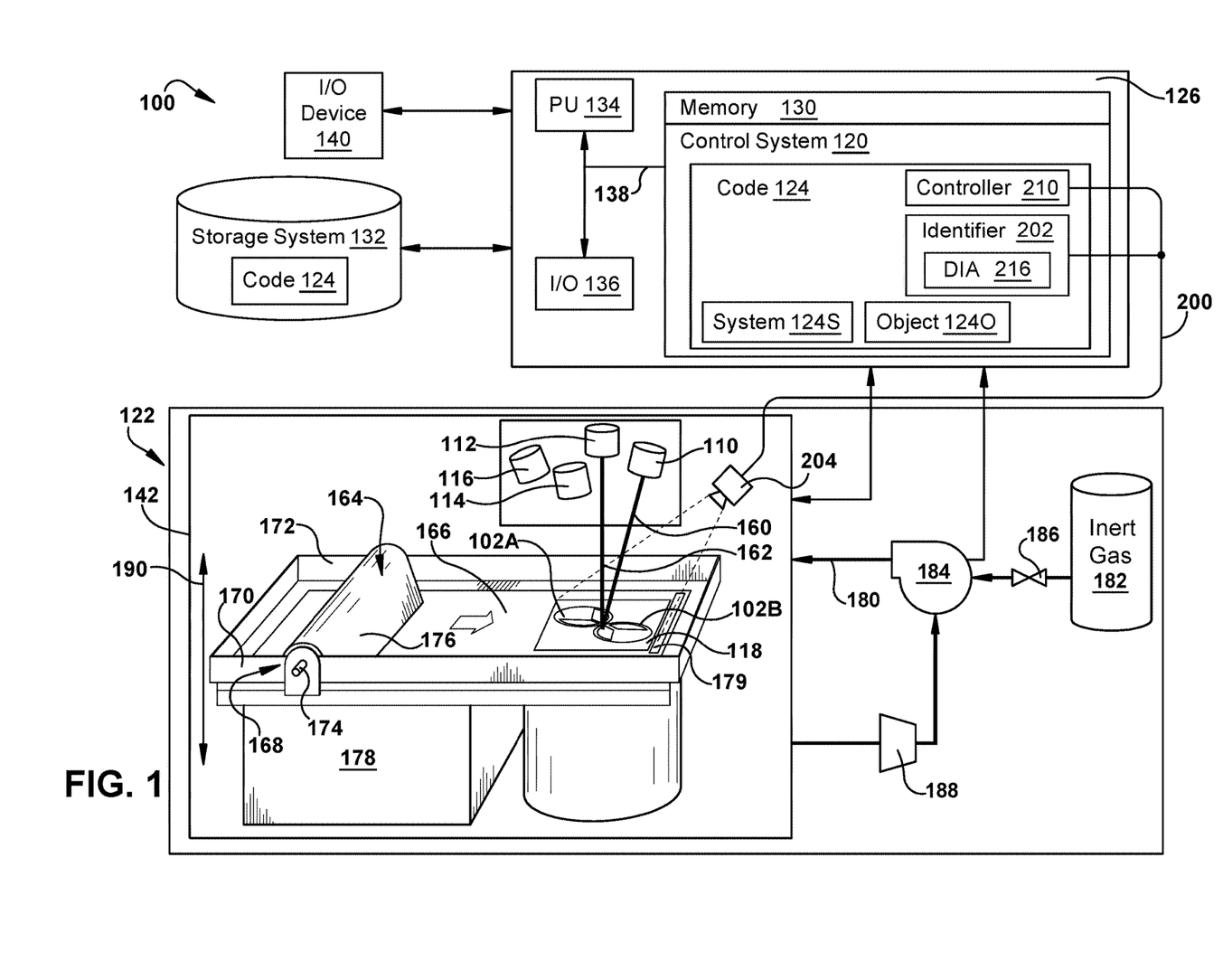
FIG. 1 shows a block diagram of an additive manufacturing process and system employing a damaged applicator identifier system according to embodiments of the disclosure.

FIG. 1 shows a schematic/block view of an illustrative computerized metal powder additive manufacturing system 100 (hereinafter 'AM system 100') for generating an object(s) 102, which may include one large object or multiple objects, e.g., two objects 102A, 102B as shown. A single layer of object(s) 102 is shown. The teachings of the disclosure will be described relative to building object(s) 102 using multiple melting beam sources, e.g., four lasers 110, 112, 114, 116, but it is emphasized and will be readily recognized that the teachings of the disclosure are equally applicable to build one object 102 or multiple object(s) 102 using any number of melting beam sources, i.e., one or more. In this example, AM system 100 is arranged for direct metal laser melting (DMLM). It is understood that the general teachings of the disclosure are equally applicable to other forms of metal powder additive manufacturing such as but not limited to direct metal laser sintering (DMLS), selective laser sintering (SLS), electron beam melting (EBM), and perhaps other forms of additive manufacturing. Object(s) 102 are illustrated as circular elements; however, it is understood that the additive manufacturing process can be readily adapted to manufacture any shaped object, a large variety of objects and a large number of objects on a build platform 118.

AM system 100 generally includes a metal powder additive manufacturing control system 120 ("control system") and an AM printer 122. As will be described, control system 120 executes set of computer-executable instructions or code 124 to generate object(s) 102 using multiple melting beam sources 110, 112, 114, 116. In the example shown, four melting beam sources may include four lasers. However, the teachings of the disclosures are applicable to any melting beam source, e.g., an electron beam, laser, etc. Control system 120 is shown implemented on computer 126 as computer program code. To this extent, computer 126 is shown including a memory 130 and/or storage system 132, a processor unit (PU) 134, an input/output (I/O) interface 136, and a bus 138. Further, computer 126 is shown in communication with an external I/O device/resource 140 and storage system 132. In general, processor unit (PU) 134 executes computer program code 124 that is stored in memory 130 and/or storage system 132. While executing computer program code 124, processor unit (PU) 134 can read and/or write data to/from memory 130, storage system 132, I/O device 140 and/or AM printer 122. Bus 138 provides a communication link between each of the components in computer 126, and I/O device 140 can comprise any device that enables a user to interact with computer 126

(e.g., keyboard, pointing device, display, etc.). Computer 126 is only representative of various possible combinations of hardware and software. For example, processor unit (PU) 134 may comprise a single processing unit, or be distributed across one or more processing units in one or more locations, e.g., on a client and server. Similarly, memory 130 and/or storage system 132 may reside at one or more physical locations. Memory 130 and/or storage system 132 can comprise any combination of various types of non-transitory computer readable storage medium including magnetic media, optical media, random access memory (RAM), read only memory (ROM), etc. Computer 126 can comprise any type of computing device such as an industrial controller, a network server, a desktop computer, a laptop, a handheld device, etc.

As noted, AM system 100 and, in particular control system 120, executes code 124 to generate object(s) 102. Code 124 can include, inter alia, a set of computer-executable instructions 124S (herein also referred to as 'code 124S' for system code, labeled 'system 124S' in FIG. 1) for operating AM printer 122 and other AM system 100 parts, and a set of computer-executable instructions 124O (herein also referred to as 'code 124O', labeled 'object 124O' in FIG. 1) defining object(s) 102 to be physically generated by AM printer 122. As described herein, additive manufacturing processes begin with a non-transitory computer readable storage medium (e.g., memory 130, storage system 132, etc.) storing code 124. Set of computer-executable instructions 124S for operating AM printer 122 may include any now known or later developed software code capable of operating AM printer 122.

Set of computer-executable instructions 124O defining object(s) 102 may include a precisely defined 3D model of an object and can be generated from any of a large variety of well-known computer aided design (CAD) software systems such as AutoCAD®, TurboCAD®, DesignCAD 3D Max, etc. In this regard, code 124O can include any now known or later developed file format. Furthermore, code 124O representative of object(s) 102 may be translated between different formats. For example, code 124O may include Standard Tessellation Language (STL) files which was created for stereolithography CAD programs of 3D Systems, or an additive manufacturing file (AMF), which is an American Society of Mechanical Engineers (ASME) standard that is an extensible markup-language (XML) based format designed to allow any CAD software to describe the shape and composition of any three-dimensional object to be fabricated on any AM printer. Code 124O representative of object(s) 102 may also be converted into a set of data signals and transmitted, received as a set of data signals and converted to code, stored, etc., as necessary. In any event, code 124O may be an input to AM system 100 and may come from a part designer, an intellectual property (IP) provider, a design company, the operator or owner of AM system 100, or from other sources. In any event, control system 120 executes code 124S and 124O, dividing object(s) 102 into a series of thin slices that assembles using AM printer 122 in successive layers of material.

AM printer 122 may include a processing chamber 142 that is sealed to provide a controlled atmosphere for object(s) 102 printing. A build platform 118, upon which object(s) 102 is/are built, is positioned within processing chamber 142. A number of melting beam sources 110, 112, 114, 116 are configured to melt layers of metal powder on build platform 118 to generate object(s) 102. While four melting beam sources 110, 112, 114, 116 will be described herein, it is emphasized that the teachings of the disclosure are applicable to a system employing any number of sources, e.g., 1, 2, 3, 5 or more.

Figure 2:
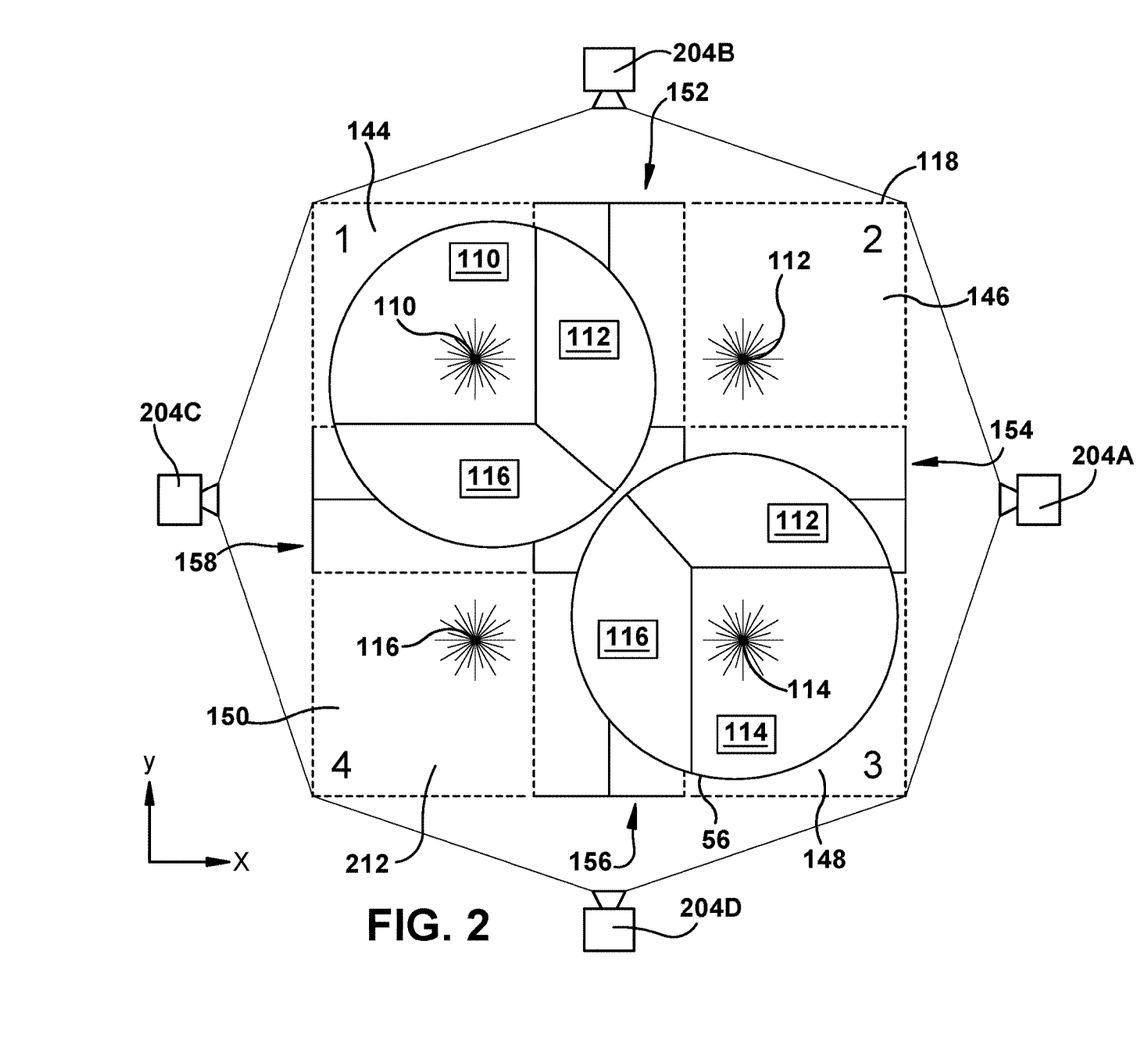
FIG. 2 shows schematic top view of a layer of raw material and including an image capture device of the damaged applicator identifier system according to embodiments of the disclosure.

As shown in the schematic plan view of FIG. 2, each melting beam source 110, 112, 114, 116 has a field 1, 2, 3 or 4 including a non-overlapping field region 144, 146, 148, 150, respectively, in which it can exclusively melt metal powder, and at least one overlapping field region 152, 154, 156, 158 in which two or more sources can melt metal powder. In this regard, each melting beam source 110, 112, 114, 116 may generate a melting beam (two shown, 160, 162, in FIG. 1), respectively, that fuses particles for each slice, as defined by code 124O. For example, in FIG. 1, melting beam source 110 is shown creating a layer of object 102 using melting beam 160 in one region, while melting beam source 112 is shown creating a layer of object 102 using melting beam 162 in another region. Each melting beam source 110, 112, 114, 116 is calibrated in any now known or later developed manner. That is, each melting beam source 110, 112, 114, 116 has had its laser or electron beam's anticipated position relative to build platform 118 correlated with its actual position in order to provide an individual position correction (not shown) to ensure its individual accuracy. In one embodiment, each of plurality melting beam sources 110, 112, 114, 116 may create melting beams, e.g., 160, 162 (FIG. 1), having the same cross-sectional dimensions (e.g., shape and size in operation), power and scan speed. Alternatively, they may have different dimensions, power and/or scan speed.

Returning to FIG. 1, an applicator 164 may create a thin layer of raw material 166 spread out as the blank canvas from which each successive slice of the final object will be created. Applicator 164 may move under control of a linear actuator system 168. Linear actuator system 168 may include any now known or later developed arrangement for moving applicator 164. In one embodiment, linear actuator system 168 may include a pair of opposing rails 170, 172 extending on opposing sides of build platform 118, and an actuator 174 such as an electric motor coupled to a transport member or body 176 of applicator 164 for moving it along rails 170, 172. Actuator 174 may be controlled by control system 120 (and damaged applicator controller 210) to move applicator 164. Other forms of linear actuator systems may also be employed. Applicator 164 can take a variety of forms. In one embodiment, applicator 164 may include transport member 176 configured to move along opposing rails 170, 172, and an actuator element 244 (FIG. 5, not shown in FIG. 1) in the form of a tip, blade or brush configured to spread metal powder evenly over build platform 118, i.e., build platform 118 or a previously formed layer of object(s) 102, to create a layer of raw material. Actuator element 244 may be coupled to transport member 176 using a holder 246 (FIG. 5, not shown in FIG. 1) in any number of ways. The process may use different raw materials 166 in the form of metal powder. Raw materials 166 may be provided to applicator 164 in a number of ways. In one embodiment, shown in FIG. 1, a stock of raw material 166 may be held in a raw material source 178 in the form of a chamber accessible by applicator 164. In other arrangements, raw material 166 may be delivered through applicator 164, e.g., through transport member 176 in front of its applicator element 244 (FIG. 5) and over build platform 118 (see, e.g., FIG. 10). Applicator element 244 (FIG. 5) can be made of a variety of materials such as but not limited to: plastic, rubber, metal, carbon fibers, ceramic, metal ceramic composite and a metal alloy. In any event, an overflow chamber 179 may be provided on a far side of applicator 164 to capture any overflow of raw material not layered on build platform 118. In FIG. 1, only one applicator 164 is shown. In some embodiments, applicator 164 may be among a plurality of applicators in which applicator 164 is an active applicator and other replacement applicators (330 in FIG. 7) are stored for use with linear transport system 168. Used or damaged applicators (338 in FIG. 7) may also be stored after they are no longer usable.

In one embodiment, object(s) 102 may be made of a metal which may include a pure metal or an alloy. In one example, the metal may include practically any non-reactive metal powder, i.e., non-explosive or non-conductive powder, such as but not limited to: a cobalt chromium molybdenum (CoCrMo) alloy, stainless steel, an austenite nickel-chromium based alloy such as a nickel-chromium-molybdenum-niobium alloy (NiCrMoNb) (e.g., Inconel 625 or Inconel 718), a nickel-chromium-iron-molybdenum alloy (NiCrFeMo) (e.g., Hastelloy® X available from Haynes International, Inc.), or a nickel-chromium-cobalt-molybdenum alloy (NiCrCoMo) (e.g., Haynes 282 available from Haynes International, Inc.), etc. In another example, the metal may include practically any metal such as but not limited to: tool steel (e.g., H13), titanium alloy (e.g., $Ti_6Al_4V$), stainless steel (e.g., 316L) cobalt-chrome alloy (e.g., CoCrMo), and aluminum alloy (e.g., $AlSi_{10}Mg$).

Processing chamber 142 is filled with an inert gas such as argon or nitrogen and controlled to minimize or eliminate oxygen. Control system 120 is configured to control a flow of an inert gas mixture 180 within processing chamber 142 from a source of inert gas 182. In this case, control system 120 may control a pump 184, and/or a flow valve system 186 for inert gas to control the content of gas mixture 180. Flow valve system 186 may include one or more computer controllable valves, flow sensors, temperature sensors, pressure sensors, etc., capable of precisely controlling flow of the particular gas. Pump 184 may be provided with or without valve system 186. Where pump 184 is omitted, inert gas may simply enter a conduit or manifold prior to introduction to processing chamber 142. Source of inert gas 182 may take the form of any conventional source for the material contained therein, e.g., a tank, reservoir or other source. Any sensors (not shown) required to measure gas mixture 180 may be provided. Gas mixture 180 may be filtered using a filter 188 in a conventional manner.

A vertical adjusting system 190 may be provided to vertically adjust a position of various parts of AM printer 122 to accommodate the addition of each new layer, e.g., a build platform 118 may lower and/or chamber 142 and/or applicator 164 may rise after each layer. Vertical adjusting system 190 may include any now known or later developed linear actuators (not shown) to provide such adjustment, and which are under the control of control system 120.

In operation, build platform 118 with metal powder thereon is provided within processing chamber 142, and control system 120 controls flow of gas mixture 190 within processing chamber 142 from source of inert gas 172. Control system 120 also controls AM printer 122, and in particular, applicator 164 (e.g., actuator 174) and melting beam sources 110, 112, 114, 116 to sequentially melt layers of metal powder on build platform 118 to generate object(s) 102 according to embodiments of the disclosure. As noted, various parts of AM printer 122 may vertically move via vertical adjustment system 190 to accommodate the addition of each new layer, e.g., a build platform 118 may lower and/or chamber 142 and/or applicator 164 may rise after each layer.

With continuing reference to FIG. 1, according to embodiments of the disclosure, AM system 100 may also include a damaged applicator identifier system 200. Damaged applicator identifier system 200 may include a damaged applicator identifier 202 configured to determine whether an active applicator, e.g., applicator 164 in FIG. 1, is damaged by identifying a non-planar surface in a test layer of raw material 166 on build platform 118 of the AM system 100 after formation of the test layer by active applicator 164. As will be described herein, damaged applicator identifier 202 may include any number of image capture devices 204 and a digital image analyzer (DIA) 216. Damaged applicator identifier system 200 may also include a damaged applicator controller 210 configured to cause replacement or repair of a damaged, active applicator in response to damaged applicator identifier 202 identifying the damaged, active applicator. As shown in FIG. 1, parts of damage applicator identifier 202 and/or damaged applicator controller 210 may be incorporated as part of control system 120, e.g., as software and/or hardware. However, each may be a separate component that interacts with control system 120 and/or parts of AM printer 122. As will be described, damaged applicator identifier system 202 may be employed with a wide variety of applicator systems 208 (see e.g., FIGS. 7, 9, 11)

In one embodiment, as shown in FIGS. 1 and 2, damaged applicator identifier 202 may include, in part, any form of image capture device 204 capable of identifying non-planar surfaces within a layer 212 of raw material applied on build platform 118. For example, damaged applicator identifier 202 may include an image capture device 204 such as but not limited to some form of digital camera. Image capture device 204 may also include any now known or later developed ancillary structure and functions necessary to its function such as but not limited to: illumination devices such as flash lighting, focus control or shutter control. Illumination devices can be placed anywhere necessary in order to illuminate or accentuate a non-planar surface in test layer 224 (FIG. 4), e.g., just above build platform 118. In one embodiment, image capture device(s) 204 is/are mounted in a stationary fashion relative to build platform 118; however, in an alternative embodiment, shown in FIGS. 9 and 10, an image capture device 204 could also be mounted to travel with an applicator 164 to capture an image of a test layer. Damaged applicator identifier 202 may include any number of image capture devices 204 necessary to capture the desired amount of detail of a layer 212 of raw material, e.g., one or more. In one embodiment, shown in FIG. 2, four image capture devices 204A, 204B, 204C, 204D are arranged around build platform 118 having layer 212 of raw material thereon. In this fashion, for each layer 212 of raw material to be captured, four images can be captured, one from each side of build platform 118. In another embodiment, shown in FIG. 3, only two image capture devices 204A, 204B are employed. In one embodiment, the images from each image capture device 204A-D of for particular layer 212 of raw material can be composited, i.e., combined, in any now known or later developed fashion, e.g., with appropriate image rotation and addition thereof using digital image analyzer (DIA) 216 of damaged applicator identifier 202. For purposes of description, all images herein are illustrated as top down. It is understood however that the images may be captured at any consistent angle between image capture device(s) 204.

Figure 3:
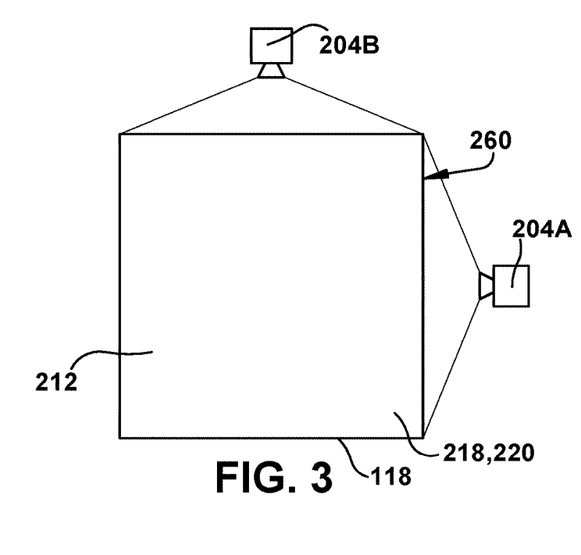
FIG. 3 shows a schematic top view of a baseline layer and a baseline image thereof for use in identifying a damaged applicator according to embodiments of the disclosure.

FIG. 3 shows a schematic view of a baseline image 218 of a baseline layer 220 of raw material on build platform 118 formed by an undamaged applicator 164 and taken by damaged applicator identifier 202. Baseline layer 218 has no defects, and hence, baseline image 218 shows no defects. That is, baseline layer 218 is substantially planar, i.e., it includes no defects sufficient to warrant repairing or replacing applicator 164. "Baseline" layer 220 and image 218 are so termed because they act as reference layer/image for identifying damaged applicators, as will be further described. A baseline image 218 of baseline layer 220 can be captured by image capture device(s) 204, for example, after a new applicator element 244 (FIG. 5) is employed for an active applicator 164 and all calibration necessary has been carried out to the satisfaction of a user that baseline layer 220 includes an ideal or close to ideal planar surface for comparison purposes to later layers that may include defects. In this case, each active applicator 164 may have a respective baseline image 218 captured once it is calibrated and considered to be creating a defect free baseline layer 220. Alternatively, a baseline image 218 can be captured for a particular new applicator 164 with new applicator element 244 and applied for a number of subsequently used, active applicators 164. In one embodiment, baseline image 218 may be a composite of images from each image capture device 204A-D of a particular baseline layer 220 of raw material, which can be formed in any now known or later developed fashion, e.g., with appropriate image rotation and addition thereof using digital image analyzer (DIA) 216 of damaged applicator identifier 202. Alternatively, it can be a single image from a single image capture device 204. In either event, baseline image(s) 220 can be stored in memory 130 and/or storage system 132 for access when necessary.

Figure 4:
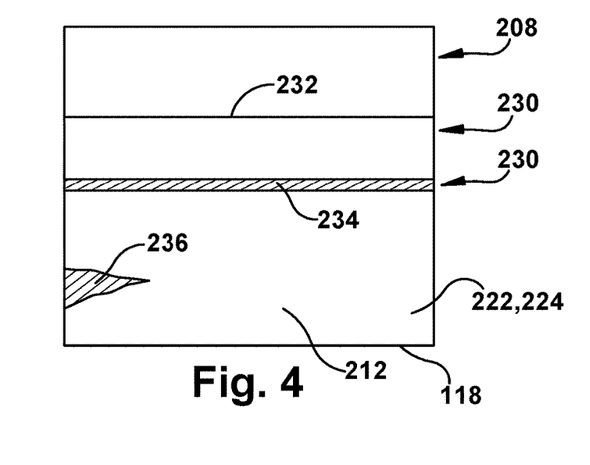
FIG. 4 shows a schematic top view of a test layer and test image for use in identifying a damaged applicator according to embodiments of the disclosure.
Figure 5:
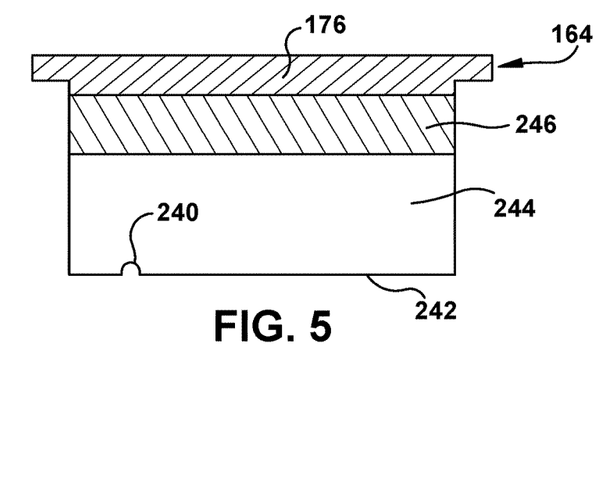
FIG. 5 shows a front view of an illustrative applicator including an applicator element and a holder therefor.

In contrast, FIG. 4 shows a schematic view of a test image 222 of a test layer 224 of raw material on build platform 118 formed by a damaged applicator 164 taken by image capture device(s) 204 of damaged applicator identifier 202. Test image 222 shows a variety defects 230. Each defect 230 creates a non-planar surface in test layer 224. "Test" layer 224 and image 222 are so termed because they are an actual layer and image thereof formed by an active applicator 164 that may include damage. Test image 222 thus may include imagery of defects 230 that can be used for identifying damaged applicators by comparison to baseline image 218, as will be further described. Defects 230 can take a variety of forms such as a raised line 232 or a raised ridge 234, each of which may extend across at least a portion if not all of test image 222. As shown in FIG. 5, raised lines 232 (FIG. 4) and/or raised ridge 234 (FIG. 4) can be formed by any of a variety of forms of opening 240 in a bottom edge 242 of applicator element 244. As noted, applicator element 244 can include a tip, brush or blade, and can be mounted in holder 246 that is coupled to transport member 176 of applicator 164. Alternatively, as shown in FIG. 4, a defect 236 may take the form of a bump or ripple formed, for example, by applicator element 244 pushing metal powder into a pile on layer 212, or defect 236 may take the form of an indentation formed, for example, by applicator element 242 causing a digging into test layer 224 (directly or indirectly). In one embodiment, test image 222 may be a composite of images from each image capture device 204A-D of for particular test layer 224 of raw material, which can be formed in any now known or later developed fashion, e.g., with appropriate image rotation and addition thereof using digital image analyzer (DIA) 216 of damaged applicator identifier 202. Alternatively, it can be a single image from a single image capture device 204. Test image 222 can be stored in memory 130 and/or storage system 132 for access when necessary. Test image 222 can be captured at any desired time during use of a particular active applicator 164, e.g., prior to initial use, after a selected number of uses, after a selected duration of use, etc.

Figure 6:
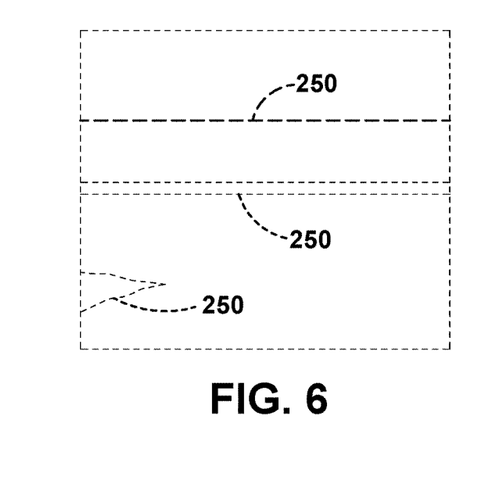
FIG. 6 shows a schematic top view of a comparison of a baseline image and a test image for use in identifying a damaged applicator according to embodiments of the disclosure.

In operation, damaged applicator identifier 202, using digital image analyzer 216, can determine whether active applicator 164 is damaged by identifying a non-planar surface, e.g., defects 230, in test layer 224 of raw material on build platform 118 of AM system 100 after formation of test layer 224 of raw material by active applicator 164. More particularly, damage applicator identifier 202 can identify the non-planar surface (FIG. 4) by comparing baseline image 218 of a surface of baseline layer 218 of raw material on build platform 118 of AM system 100 after formation of the baseline layer 218 by an undamaged applicator 164 to test image 222 of test layer 224 of raw material on build platform 118 of AM system 100 after formation of test layer 224 by active applicator 164. As noted, each of baseline image 218 and test image 222 may be composite images formed from a number of image captures from a plurality of sides about respective baseline layer 220 or test layer 224. A variety of now known techniques are available to identify differences between images so that defects 230 can be identified, all of which are considered within the scope of the disclosure. In one example, the comparing may include determining a number of pixels remaining after subtracting baseline image 222 from test image 218, and identifying existence of the non-planar surface, i.e., defects 230 and damaged applicator 164, in response to the number of pixels exceeding a threshold. The threshold can be user selected to be any number of pixels sufficient to indicate the presence of defects 230 (FIG. 4), a non-planer surface in test layer 224 and thus a damaged applicator 164. FIG. 6 shows a schematic top view of the result of comparing baseline image 218 (FIG. 3) to test image 222 (FIG. 4), resulting in pixels 250 remaining of the images from some of defects 232, 234, 236. In the example shown, defect 232 (FIG. 4) shows a number of pixels to perhaps exceed a threshold, while defects 234, 236 may not have sufficient pixel numbers to exceed a threshold. It is emphasized that a variety of alternative techniques may be employed other than pixel counting to determine the presence of a non-planar surface in test layer 224 sufficient to indicate a damaged applicator. In any event, the comparison can be carried out at any desired time during use of a particular active applicator 164, e.g., after a selected number of uses, after a selected duration of use, etc.

Referring to FIGS. 7-12, damaged applicator controller 210 (FIG. 1) of AM system 100 may interact with a variety of applicator systems 208 to replace or repair a damaged applicator. As will be described, in response to damaged applicator identifier 202 identifying a damaged, active applicator 328 (FIG. 7) damaged applicator controller 210 may cause replacement or repair of the damaged, active applicator 328 (FIG. 7), using one of the systems to be described hereafter.

Figure 7:
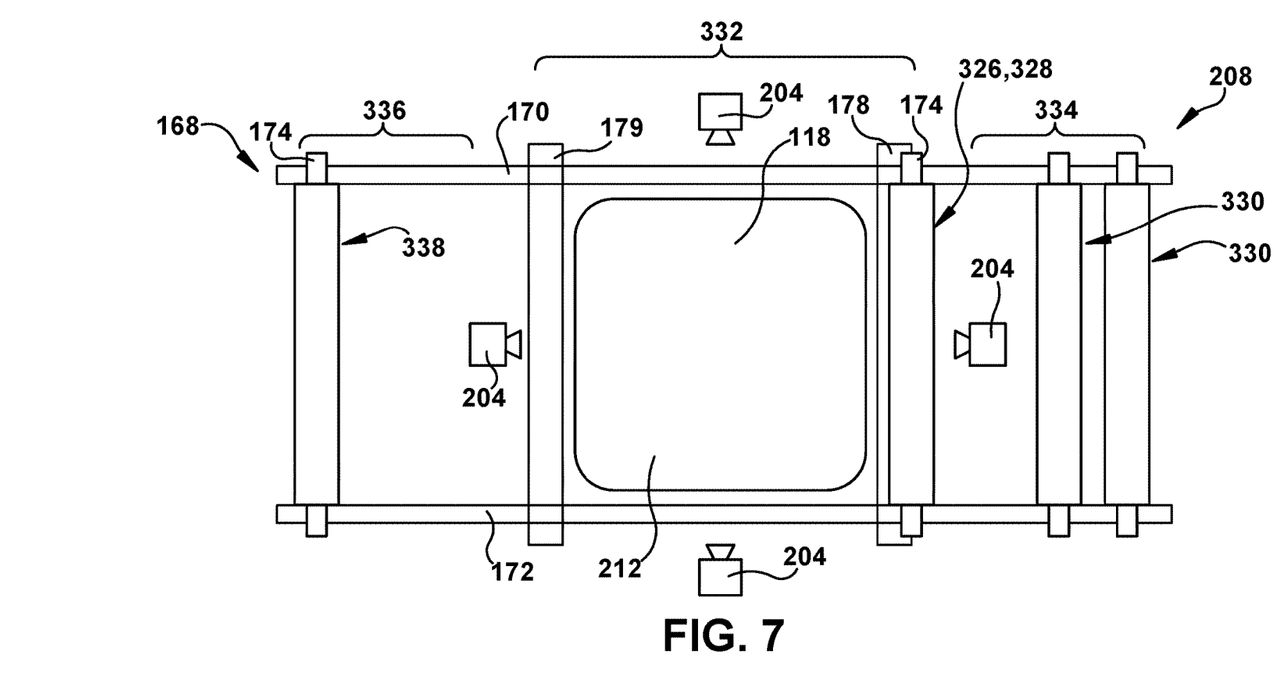
Figure 8:
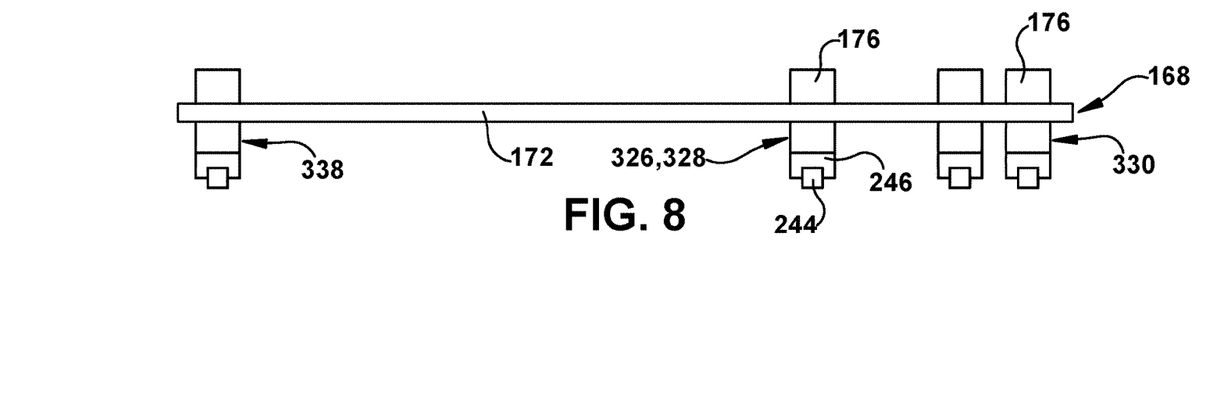
FIG. 8 shows a schematic side view of an applicator system including replacement applicators according to an embodiment of the disclosure.

In FIGS. 7 and 8, AM system 100 may employ a plurality of applicators including an active applicator 326, i.e., that is in use (as in FIG. 1), and at least one replacement applicator 330 (two shown) for replacing a damaged, active applicator 328 (shown as same as active applicator 326). In FIGS. 7 and 8, damaged applicator 328 can be replaced with a replacement applicator 330. FIG. 7 shows a schematic top view and FIG. 8 shows a schematic side view of a linear actuator system 168 including the plurality of applicators. In this embodiment, each applicator 326, 328, 330 may be structured as described previously relative to applicator 164 in FIG. 1, e.g., each applicator 326, 328, 330 may include its own actuator 174 for controlled movement along rails 170, 172 under control of damage applicator controller 210 (perhaps with control system 120) (FIG. 1). That is, as shown best in FIG. 7, active applicator 326 and each replacement activator 330 may be positioned relative to build platform 118 with linear actuator system 168, e.g., using rails 170, 172 and respective actuators 174, under control of damaged applicator controller 210 (FIG. 1). In this case, linear actuator system 168 includes an active applicator area 332 in which active applicator 326 is movable over source of raw material 178 and build platform 118 to apply layer 212 of raw material on build platform 118, and a replacement applicator storage area 334 in which each replacement applicator 330 is inoperatively (ready, but not in use) stored prior to replacing damaged, active applicator 328. Each area 332, 334 may be, for example, indicative of a location on rails 170, 172. Linear actuator system 168 may further include a used applicator storage area 336 in which at least one damaged, active applicator 338 is stored after replacement by a replacement applicator 330. In operation, upon damaged applicator identifier 202 identifying a damaged applicator 328, damaged applicator controller 210 directs damaged applicator 328 to be moved to used applicator storage area 336 for storage, and a new replacement applicator 330 to be put into service as active applicator 326. This process can repeat as many time as necessary (supply of replacement applicators withstanding) during operation of AM system 100 to ensure an undamaged applicator is always in service.

Figure 9:
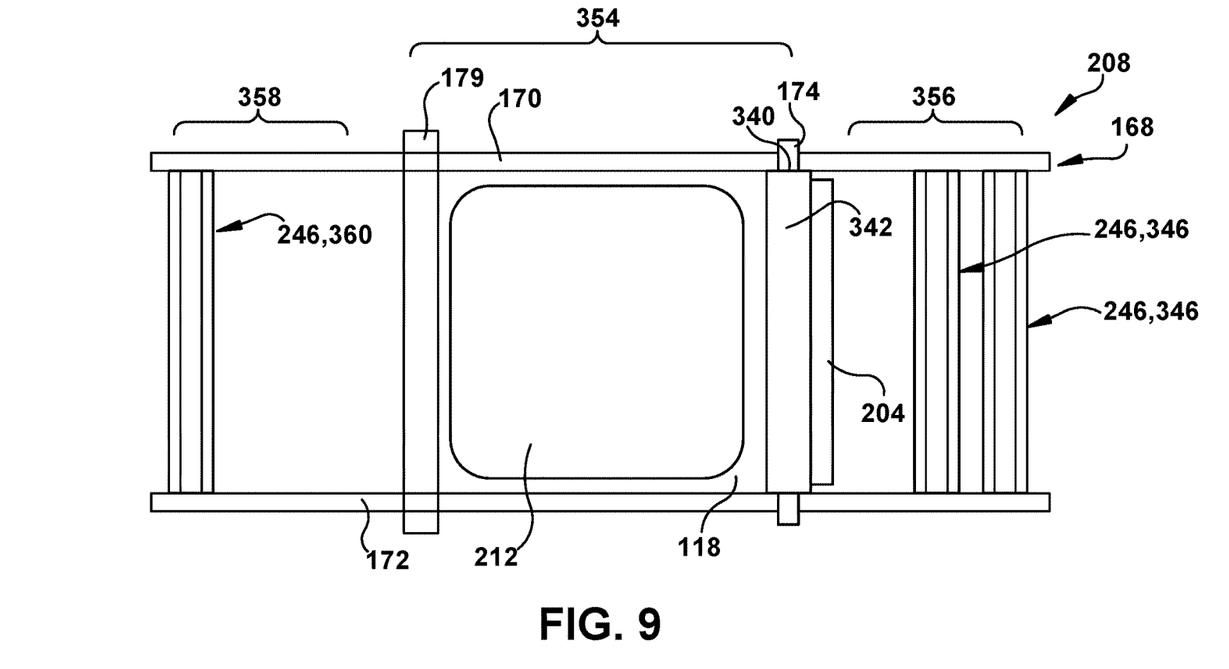
Figure 10:
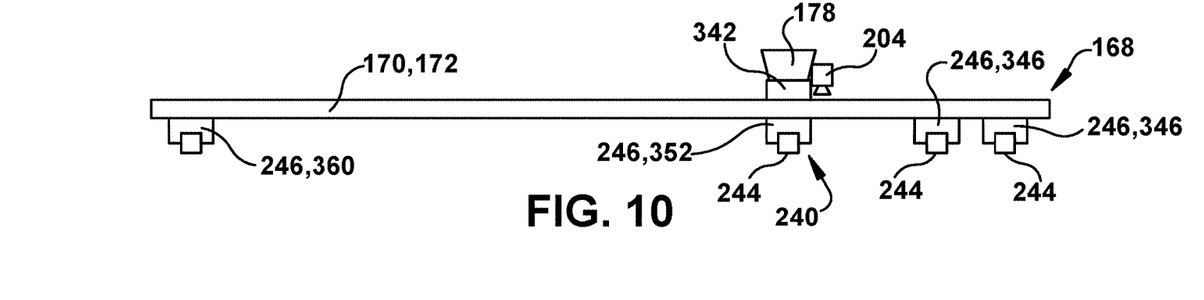
FIG. 10 shows a schematic side view of an applicator system including replacement applicator element holders according to an embodiment of the disclosure.

Referring to FIGS. 9 and 10, in an alternative embodiment, AM system 100 may employ an active applicator 340 including a single transport member 342. FIG. 9 shows a schematic top view and FIG. 10 shows a schematic side view of linear actuator system 168 including active applicator 340 having single transport member 342. (In the FIG. 10 example, raw material source 178 is carried with single transport member 342.) Active applicator 340 may be structured as described previously relative to applicator 164 in FIG. 1, e.g., it may include its own actuator 174 under control of control system 120 (and controller 210) (FIG. 1), except here, single transport member 342 is capable of selective coupling to a number of applicator holders 246, each having a respective applicator element 244 thereon. That is, single transport member 342 can couple to, and decouple, from any one of a number of applicator holders 246. The coupling may be made using any now known or later developed coupling system (not shown) such as but not limited: an opening/closing grasping arrangement, a magnetic or electromagnetic arrangement or a male-female sliding arrangement. As shown best in FIG. 9, single transport member 342 forms active applicator 340 with a selected, active applicator holder 352, and at least one replacement applicator holder 346 (two shown) is stored for later use. Single transport member 242 may be positioned relative to build platform 118 with linear actuator system 168, e.g., using rails 170, 172 and a single linear actuator 174, under control of damaged applicator controller 210 (and control system 120) (FIG. 1). In this case, linear actuator system 168 includes an active applicator area 354 in which active applicator 340 is movable over source of raw material 178 and build platform 118 to apply layer 212 of raw material on build platform 118, and a replacement applicator holder storage area 356 in which each replacement applicator holder(s) 346 is inoperatively (ready, but not in use) stored prior to replacing a damaged, active applicator holder 252. Each area 354, 356 may be, for example, indicative of a location on rails 170, 172. Linear actuator system 168 may further include a used applicator holder storage area 358 in which at least one damaged applicator holder 360 is stored after replacement by a replacement applicator holder 346. In operation, upon damaged applicator identifier 202 identifying damaged applicator 328, damaged applicator controller 210 moves transport member 342 to used applicator holder area 358 and decouples holder 352. Damaged applicator controller 210 then moves transport member 342 to replacement applicator holder storage area 356, and directs coupling of transport member 342 to a replacement applicator holder 346, forming a new active applicator 340. This process can repeat as many time as necessary (supply of replacement holders withstanding) during operation of AM system 100 to ensure an undamaged applicator is always in service.

Figures 11, 12, 13:
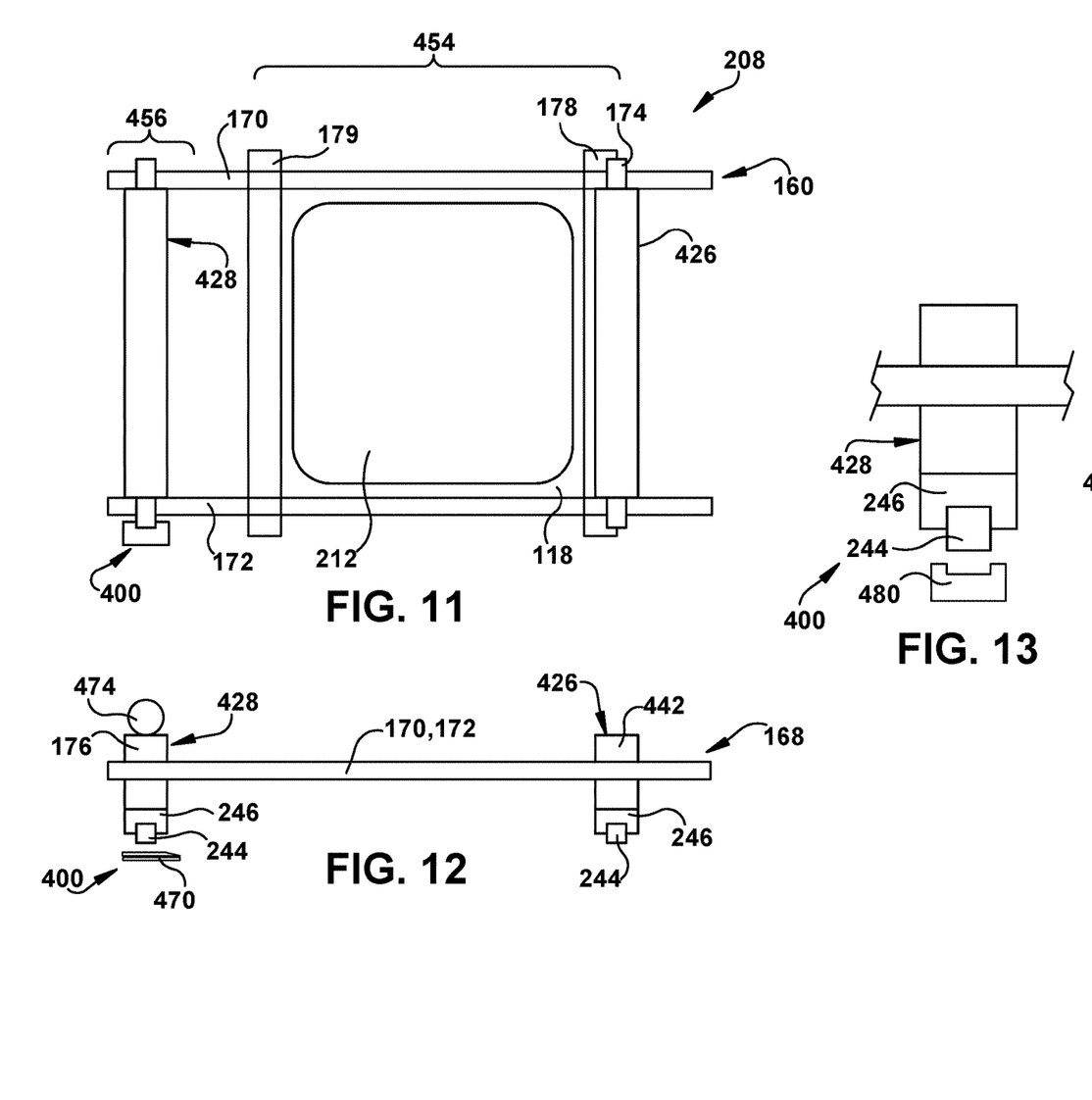

Turning to FIG. 11-14, in another embodiment, AM system 100 may employ a repair device 400 for repairing a damaged, active applicator 428. FIG. 11 shows a schematic top view and FIG. 12 shows a schematic side view of linear actuator system 168 including and active applicator 426. An active applicator 426 may be structured as described previously relative to applicator 164 in FIG. 1, e.g., it may include its own actuator 174 under control of control system 120 (and controller 210) (FIG. 1). That is, active applicator 426 may be positioned relative to build platform 118 and repair device 400 with linear actuator system 168 under control of damaged applicator controller 210 (and control system 120) (FIG. 1). In this case, linear actuator system 168 includes an active applicator area 454 in which active applicator 426 is movable over source of raw material 178 and build platform 118 to apply layer 212 of raw material on build platform 118, and a repair area 456 in which a damaged, active applicator 428 is accessible to repair device 400. Each area 454, 456 may be, for example, indicative of a location on rails 170, 172. In this embodiment, where damaged applicator identifier 202 identifies active applicator 426 as a damaged applicator 428 (i.e., creating a non-planar surface with defects 230 (FIG. 4)), damaged applicator control 210 directs linear transport system 168 to move damaged applicator 428 to repair area 456, and directs repair device 400 repairs applicator element 244.

Figure 14:
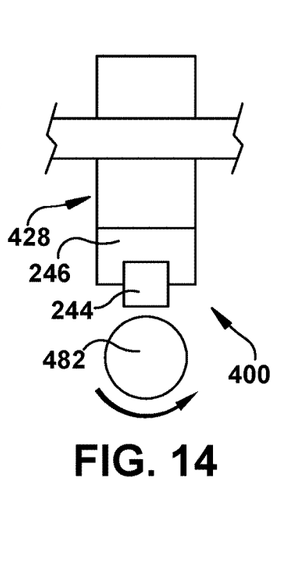

As shown in FIGS. 12-14, repair device 400 can take a variety of forms depending on the form of applicator element 244 employed on active applicator 426. In FIG. 12, applicator element 244 may include a plastic or polymer material. In this case, repair device 400 includes a cutting device 470, e.g., a cutting blade, configured to cutoff a damaged portion of applicator element 244 in such a way as to provide a clean new surface therefor. The repaired applicator can then be put back into surface by damaged applicator controller 210, perhaps after some re-calibration, as an active applicator 426. Where applicator element 244 includes a plastic or polymer, a roll of applicator element 474 may be provided on active applicator 426, i.e., on transport member 176, for feeding additional applicator element material through holder 246 as it is used up. In FIG. 13, applicator element 244 may include a moldable material, e.g., a soft plastic, rubber or polymer. In this case, repair device 400 may include a molding device 480, e.g., a shaped heating element, configured to re-shaped a damaged portion of applicator element 244 in such a way as to provide a clean new surface therefore. The repaired applicator can then be put back into surface, perhaps after some re-calibration, as an active applicator 426. In FIG. 14, applicator element 244 may include a blade, e.g., a metal or metal alloy blade. In this case, repair device 400 may include a grinding device 482, e.g., a grinding wheel or belt, configured to grind a damaged portion of applicator element 244 in such a way as to provide a clean new surface therefore. The repaired applicator can then be put back into surface, perhaps after some re-calibration, as an active applicator 426. Repair device 400 may include any ancillary control structures (not shown) necessary for controlled application thereof by damaged applicator controller 210 such as but not limited to: motion controllers; sensor(s) for positioning, force, temperature, etc.; or quality assurance monitors. In operation, upon damaged applicator identifier 202 identifying damaged applicator 328, damaged applicator controller 210 moves damaged applicator 428 to repair area 456 and causes repair device 400 to repair the damaged applicator. Once repaired, damaged applicator controller 210 then puts the applicator back in service. This process can repeat as many time as necessary (applicator element material capability of repair withstanding) during operation of AM system 100 to ensure an undamaged applicator is always in service.

Another embodiment of the disclosure may include AM system 100 including build platform 118 (FIG. 1), and a melting beam source(s) 110, 112, 114, 116 (FIG. 1) for sequentially building an object 102 layer by layer on build platform 118. AM system 100 may also include a raw material source 178 operatively coupled to build platform for providing raw material to build platform for the sequential building, i.e., as a hopper for accessing by an active applicator or carried by an active applicator (see e.g., FIG. 10). AM system 100 further includes an applicator system 208 (any applicator system described herein) operative to apply layer 212 of the raw material on build platform 118 from the raw material source using an active applicator. In one embodiment, as shown in FIGS. 7 and 8, applicator system 208 may include a plurality of applicators including active applicator 326 and at least one replacement applicator 330 for replacing a damaged, active applicator 328, each replacement applicator 330 including an undamaged applicator element. In any event, linear actuator system 168 may move applicators, as discussed herein. AM system 100 may also include damaged applicator identifier 202, as described herein, for determining whether the active applicator is damaged by identifying a non-planar surface in a layer of raw material on the build platform after formation of the layer by the active applicator, and damaged applicator controller 210 configured to cause replacement or repair of the damaged, active applicator in response to the damaged applicator identifier identifying the damaged, active applicator.

Embodiments of the disclosure thus provide a damaged applicator identifier system 200 capable of detecting a damaged applicator (applicator element in the form of a blade, brush or lip/wiper) from digital image analysis of the defective layer of raw material on the build platform. Consequently, embodiments of the disclosure do not simply analyze a potentially damaged applicator, but evaluate an actual layer of raw material created by a potentially damaged applicator, which provide a better understanding of actual applicator damage. Any of the embodiments described herein can operate during an object build to repair an active applicator during the build. (The entire system is located within process chamber 142 (FIG. 1)). The damaged applicator can be replaced and moved to a used storage area or can be repaired. Once a repaired or replaced applicator is in place, an object build can proceed as originally intended unless another instance of application damage was to occur, then at that time, AM system 100 would once again perform the previously described procedure to procure an undamaged active applicator. Embodiments of the disclosure are able to minimize a defect to only the region of the build that caused it without passing it to the entirety of the remainder of the build, and without canceling a build or opening the process chamber. Consequently, a particular object build now has a better chance of recovering the build when a damaged applicator issue arises rather than having to cancel it at the time of applicator damage, or scrap the applicator after the build completes.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise. "Approximately" as applied to a particular value of a range applies to both values, and unless otherwise dependent on the precision of the instrument measuring the value, may indicate +/−10% of the stated value(s).

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. A damaged applicator identifier system for an additive manufacturing (AM) system, the damaged applicator identifier system comprising:
 a damaged applicator identifier configured to determine whether an active applicator is damaged by identifying a non-planar surface in a test layer of raw material on a build platform of the AM system after formation of the test layer by the active applicator; and
 a damaged applicator controller configured to:
  cause replacement or repair of the damaged, active applicator in response to the damaged applicator identifier identifying the non-planar surface in the test layer indicative of the damaged, active applicator, and cause an applicator system to manufacture an object after causing replacement or repair of the damaged, active applicator, wherein the object does not include the test layer.

2. The system of claim 1, wherein the damaged applicator identifier includes an image capturing device.

3. The system of claim 2, wherein the damage applicator identifier identifies the non-planar surface by comparing a baseline image of a surface of a baseline layer of raw material on the build platform of the AM system after formation of the baseline layer by an undamaged applicator to a test image of the layer of raw material on the build platform of the AM system after formation of the layer by the active applicator.

4. The system of claim 3, wherein each of the baseline image and the test image are composite images formed from a number of image captures from a plurality of sides about the respective baseline layer or test layer.

5. The system of claim 3, wherein the comparing further includes determining a number of pixels remaining after subtracting the baseline image from the test image, and the identifying the non-planar surface in response to the number of pixels exceeding a threshold.

6. The system of claim 1, further comprising at least one replacement applicator for replacing the damaged, active applicator, and wherein the active applicator and each replacement activator are positioned relative to the build platform with a linear actuator system under control of the damaged applicator controller.

7. The system of claim 6, wherein the linear actuator system includes:
an active applicator area in which the active applicator is movable over the source of raw material and the build platform to apply the layer of the raw material on the build platform; and
a replacement applicator storage area in which each replacement applicator is inoperatively stored prior to replacing the damaged, active applicator.

8. The system of claim 7, wherein the linear actuator system further includes a used applicator storage area in which at least one damaged, active applicator is stored after replacement by a replacement applicator.

9. The system of claim 1, further comprising a repair device for repairing the damaged, active applicator, and wherein the active applicator is positioned relative to the build platform and the repair device with a linear actuator system under control of the damaged applicator controller.

10. The system of claim 9, wherein the linear actuator system includes:
an active applicator area in which the active applicator is movable relative to the build platform to apply the layer of the raw material on the build platform from the raw material source; and
a repair area in which the damaged, active applicator is accessible to the repair device.

11. An additive manufacturing (AM) system, comprising:
a build platform;
a melting beam source for sequentially building an object layer by layer on the build platform;
a raw material source operatively coupled to the build platform for providing raw material to the build platform for the sequential building;
an applicator system operative to apply a layer of the raw material on the build platform from the raw material source using an active applicator;
a damaged applicator identifier configured to determine whether the active applicator is damaged by identifying a non-planar surface in a test layer of raw material on a build platform of the AM system after formation of the test layer by the active applicator; and
a damaged applicator controller configured to cause replacement or repair of the damaged, active applicator in response to the damaged applicator identifier identifying the non-planar surface in the test layer indicative of the damaged, active applicator;
wherein the applicator system is further configured to manufacture an object after the replacement or repair of the damaged, active applicator, and the object does not include the test layer.

12. The AM system of claim 11, wherein the damaged applicator identifier includes an image capturing device.

13. The AM system of claim 12, wherein the damage applicator identifier identifies the non-planar surface by comparing a baseline image of a surface of a baseline layer of raw material on the build platform of the AM system after formation of the baseline layer by an undamaged applicator to a test image of the layer of raw material on the build platform of the AM system after formation of the layer by the active applicator.

14. The AM system of claim 13, wherein each of the baseline image and the test image are composite images formed from a number of image captures from a plurality of sides about the respective baseline layer or test layer.

15. The AM system of claim 13, wherein the comparing further includes determining a number of pixels remaining after subtracting the baseline image from the test image, and the identifying the non-planar surface in response to the number of pixels exceeding a threshold.

16. The AM system of claim 11, wherein the applicator system includes a plurality of applicators including the active applicator and at least one replacement applicator for replacing the damaged, active applicator, each replacement applicator including an undamaged applicator element, and
wherein the damaged applicator controller causes replacement of the damaged, active applicator with one of the at least one replacement applicators in response to the damaged applicator identifier identifying the damaged, active applicator.

17. The AM system of claim 16, wherein the active applicator and each replacement activator are positioned relative to the raw material source and the build platform with a linear actuator system under control of the damaged applicator controller, wherein the linear actuator system includes:
an active applicator area in which the active applicator is movable relative to the build platform to apply the layer of the raw material on the build platform from the raw material source; and
a replacement applicator storage area in which each replacement applicator is inoperatively stored prior to replacing a damaged, active applicator.

18. The AM system of claim 11, wherein the linear actuator system further includes a used applicator storage area in which at least one damaged, active applicator is stored after replacement by a replacement applicator.

19. The AM system of claim 18, wherein the active applicator is positioned relative to the build platform with a linear actuator system under control of the damaged applicator controller, wherein the linear actuator system includes:

an active applicator area in which the active applicator is movable relative to the build platform to apply the layer of the raw material on the build platform from the raw material source; and a repair area in which a repair of the damaged, active applicator occurs.

20. An additive manufacturing (AM) system, comprising:

a build platform;

a melting beam source for sequentially building an object layer by layer on the build platform;

a raw material source operatively coupled to the build platform for providing raw material to the build platform for the sequential building;

an applicator system operative to apply a layer of the raw material on the build platform from the raw material source, the applicator system including a plurality of applicators including an active applicator and at least one replacement applicator for replacing a damaged, active applicator, each replacement applicator including an undamaged applicator element;

a damaged applicator identifier configured to determine whether the active applicator is damaged by identifying a non-planar surface in a test layer of raw material on a build platform of the AM system after formation of the test layer by the active applicator; and a damaged applicator controller configured to:

cause replacement or repair of the damaged, active applicator in response to the damaged applicator identifier identifying the non-planar surface in the test layer indicative of the damaged, active applicator;

wherein the applicator system is further configured to manufacture an object after the damaged applicator controller causes replacement or repair of the damaged, active applicator, and the object does not include the test layer.

* * * * *